(12) United States Patent
Colby et al.

(10) Patent No.: US 6,783,740 B2
(45) Date of Patent: Aug. 31, 2004

(54) SINTERED GLASS BEAD FILTER WITH ACTIVE MICROBIAL DESTRUCTION

(75) Inventors: Mary W. Colby, West Hartford, CT (US); Andre E. Berghmans, Bethpagen, NY (US); Donald DiMarzio, Northport, NY (US); Ronald Pirich, Islip, NY (US)

(73) Assignee: Northrop Grumman Corporation, Los Angeles, CA (US)

( * ) Notice: Subject to any disclaimer, the term of this patent is extended or adjusted under 35 U.S.C. 154(b) by 76 days.

(21) Appl. No.: 10/261,268

(22) Filed: Sep. 30, 2002

(65) Prior Publication Data

US 2004/0071612 A1 Apr. 15, 2004

(51) Int. Cl.$^7$ ................................................. B01J 19/08
(52) U.S. Cl. ....................... 422/186.3; 422/121; 422/24
(58) Field of Search ............................. 422/186.3, 121, 422/24

(56) References Cited

U.S. PATENT DOCUMENTS

| | | |
|---|---|---|
| 3,202,733 A | 8/1965 | Strauss |
| 3,564,081 A | 2/1971 | Francois et al. |
| 4,278,632 A | 7/1981 | Yoldas |
| 4,317,668 A | 3/1982 | Susa et al. |
| 4,430,108 A | 2/1984 | Hojaji et al. |
| 4,678,758 A | 7/1987 | Kampfer et al. |
| 4,682,992 A | 7/1987 | Fuchs |
| 4,777,153 A | 10/1988 | Sonuparlak et al. |
| 4,966,759 A | 10/1990 | Robertson et al. |
| 5,059,366 A | 10/1991 | Galaj et al. |
| 5,063,003 A | 11/1991 | Gonzalez-Oliver |
| 5,163,626 A | 11/1992 | Urwin et al. |
| 5,175,199 A | 12/1992 | Asano et al. |
| 5,194,161 A | 3/1993 | Heller et al. |
| 5,256,616 A | 10/1993 | Heller et al. |
| 5,308,458 A | 5/1994 | Urwin et al. |
| 5,658,530 A | 8/1997 | Dunn |
| 5,753,322 A | 5/1998 | Yamaguchi et al. |
| 5,881,353 A * | 3/1999 | Kamigata et al. ............... 419/2 |
| 5,933,702 A * | 8/1999 | Goswami .................. 422/186.3 |
| 5,942,280 A | 8/1999 | Mathers et al. |
| 6,235,351 B1 | 5/2001 | DiMarzio et al. |

FOREIGN PATENT DOCUMENTS

RU     2151632 C   *   6/2000

* cited by examiner

Primary Examiner—Kishor Mayekar
(74) Attorney, Agent, or Firm—Stetina Brunda Garred & Brucker (57) ABSTRACT

A microbicidal filter system having superior drop pressure and low complexity is provided, as well as a method for producing the same. The system comprises a plurality of glass beads having pores formed therebetween for the flow of air therethrough. The sintered glass beads are coated in a transition metal oxide and water. An ultraviolet light source is used to cause a photocatalytic reaction between the transition metal oxide and water. Free hydroxyl radicals with microbicidal properties are produced. Urethane foam may be inserted between the glass beads before sintering in order to cause a bimodal pore size distribution, and particulates disposed on the glass beads may be added to alter surface activity.

25 Claims, 6 Drawing Sheets

SINTERED GLASS BEAD FILTER WITH ACTIVE MICROBIAL DESTRUCTION

STATEMENT RE: FEDERALLY SPONSORED RESEARCH/DEVELOPMENT

The present invention was conceived under Government Contract No. PEPS N65236-98-C-5820. The Government has certain rights in this invention.

CROSS-REFERENCE TO RELATED APPLICATIONS (Not Applicable)

BACKGROUND OF THE INVENTION

The present invention relates generally to air filtering systems, and more particularly to a sintered glass bead filter with active destruction capability for filtering microcontaminants from air to be breathed by humans.

Air filtering systems are important for healthy breathing in a number of environments and in a number of applications. For instance, large office buildings must incorporate air filtering systems designed to ensure that the air recycled within a building is clean, in order to protect the health of the people in the building. Hospitals must use air filtering systems to isolate weakened patients from pathogens, or isolate patients with contageous illnesses from other patients. Also, the rising incidence of terrorism in the United States has created awareness of the increasingly present possibility that civilian populations will be intentionally targeted with biological weapons in the near future. Of course, air filtering systems are particularly important to military personnel, who regularly operate in arenas where exposure to natural or artificial microcontaminants is a particularly real possibility. In each of these situations, the welfare or even the lives of the people involved depend entirely upon the quality of the air filtering equipment at their disposal. Accordingly, it is important that air filtering systems continue to advance to meet the new challenges posed as the world becomes a more complicated and dangerous place.

Prior art air filtering systems take variety of embodiments. The simplest kind of filter is a physical filter. The simple physical filter is composed of a fabric or other porous material. The pores of the material must be smaller than contaminants to be filtered, but large enough to allow air passage. If they are, the contaminants will be blocked, and only the clean portion of the air will pass the filter. Obvious disadvantages of the physical filter are the speed with which the filter becomes clogged, and therefore useless, and the fact that physical filters generally cannot screen particles of below a certain size.

A more advanced type of filter is the activated carbon filter. Activated carbon filters comprise a highly porous activated carbon element, the cavities of which effectively draw in contaminants by means of both London Force and electrostatic force in a kind of capillary action. Activated carbon filters are substantially more effective than simple physical filters at trapping many kinds of small contaminants. However, certain contaminants will still evade activated carbon filters.

Another more advanced type of filter is the ionic filter. Ionic filters produce negatively charged ions which attach to particles in the air. The air is then passed through a positively charged filter. The negatively charged ions are drawn toward the positive charge and carry the attached particles with them, removing them from the air as it passes through the positively charged filter. Like activated carbon filters, ionic filters are more effective against certain microcontaminants than simple physical filters, but still fail to neutralize others.

Still another advanced type of filter is the High Efficiency Particle Arrest (HEPA) filter. HEPA filters employ a glass fiber filter which is pleated in such a way that the actual surface area over which air passes is very large in comparison to the volume occupied by the filter. The large surface area results in a decreased pressure drop across the filter, or in other words, it is easier for air to pass through the filter. In its simplest form, the HEPA filter is essentially an advanced physical filter.

Modern mechanical filters generally employ multiple levels of filtering, often using more than one of the above mentioned methods in sequence. Complicated mechanical filters reach high levels of effectiveness in filtering air, but have the disadvantage of being too complicated for use in many applications.

In addition to any other drawbacks, all of the above mentioned filters suffer from the common drawback that they become clogged with contaminants over time, resulting in an air pressure drop across the filter. In other words, as the filter is used, it becomes more and more difficult to pass air through it. A recent technology for eliminating contaminants which addresses this problem involves using a transition metal oxide and water in conjunction with an ultraviolet light source in order to create free hydroxyl groups with microbicidal properties. This method is described in U.S. Pat. No. 5,933,702 PHOTOCATALYTIC AIR DISINFECTION issued to Goswami ("Goswami"). Ultraviolet light is cast upon a transition metal oxide in the presence of water. In response, the transition metal oxide undergoes a photocatalytic reaction with the water, thereby producing free hydroxyl radicals. The hydroxyl radicals react with contaminants, rendering them neutral.

The above described method has been put to use in a variety of applications. U.S. Pat. No. 6,235,351 METHOD FOR PRODUCING A SELF DECONTAMINATING SURFACE issued to DiMarzio et al. discloses surfaces which employ the method to become self decontaminating when exposed to ultraviolet light. Goswami discloses air filters made using the method. However, prior art photocatalytic disinfection systems have suffered from the drawback that because exposure to ultraviolet light is necessary for proper functionality, it was impossible to manufacture filters which combined the benefits of high surface area for minimum pressure drop and maximum simplicity in design with respect to lighting sources and manufacturing complexity. Accordingly, a need exists to devise a photocatalytic filtering system which can combine these features in order to make photocatalytic filtering more effective and bring it into broader applicability.

BRIEF SUMMARY OF THE INVENTION

It is therefore an object of the present invention to provide a photocatalytic filtering system free of the aforementioned drawbacks. The filter system comprises a plurality of sintered glass beads having pores formed therebetween for the passage of air therethrough. In the preferred embodiment, the sintered glass beads are sintered at a temperature of above a transition temperature of the glass beads. Sintering at above the transition temperature ensures that a degree of crystalization within the glass beads is under a selected threshold. Crystal formation reduces transmissiveness, so the selected threshold is selected so that ultraviolet light can penetrate the glass beads to a selected depth in order to ensure that all the glass beads can be illuminated.

The sintered glass beads essentially form a highly microporous glass structure. The surface area of the glass beads per thickness of the structure is high compared to what it would be if there were no pores formed therebetween. Because pressure drop is inversely proportional to the surface area of the glass beads, the pressure drop characteristic of the filter system benefits thereby. Air follows a tortuous path between the glass beads while being filtered as described below. Depending on the size of the pores, the sintered glass beads may also act as a physical filter.

The filter system further comprises a coating formed on the glass beads of transition metal oxide, such as $TiO_2$, and water. The water can be provided by ambient humidity or artificial humidification. An ultraviolet light source is also comprised by the system, and may be the sun or an artificial source. It is used to cast ultraviolet light upon the glass beads. Because the glass beads are substantially transmissive of ultraviolet light, at least some ultraviolet light will pass the more proximate glass beads to reach the more distal glass beads. Accordingly, the surface area of all the glass beads is illuminated. The ultraviolet light causes a photocatalysis reaction between the titanium oxide and the water of the coating, producing free hydroxyl radicals with microbicidal properties. The hydroxyl radicals accomplish the active destruction of microcontaminants.

The filter of the filter system may be configured advantageously through methods known to those in the art. For instance, the filter may be designed as a hollow cylinder. The hollow cylinder design has a high surface area compared to that of other possible shapes, reducing pressure drop. If the pressure drop of the filter is below 40 mm $H_2O$ at 85 liters per minute, unassisted human breathing through the filter is possible. A filter of this shape with 2 cm walls and a 15 cm height proved to have a pressure drop well within this limit while retaining above 98% capture efficiency at all face velocities.

In accordance with a further embodiment, urethane foam is inserted between the glass beads prior to sintering. During sintering, the urethane foam decomposes and oxidizes. The result of using urethane foam is a bimodal pore size distribution. The paths between the glass beads appear to take more tortuous paths when there are both large and small pores, increasing capture efficiency In still another embodiment, particulates disposed on the glass beads are also comprised by the filter system. The particulates can be, for instance, glass particulates or chopped fibers. The particulates alter the surface activity of the filter system, and may increase capture efficiency in certain applications.

BRIEF DESCRIPTION OF THE DRAWINGS

FIG. 2b is a cross-sectional view of a glass bead 12, showing in FIG. 2a

DETAILED DESCRIPTION OF THE INVENTION

Figure 1:
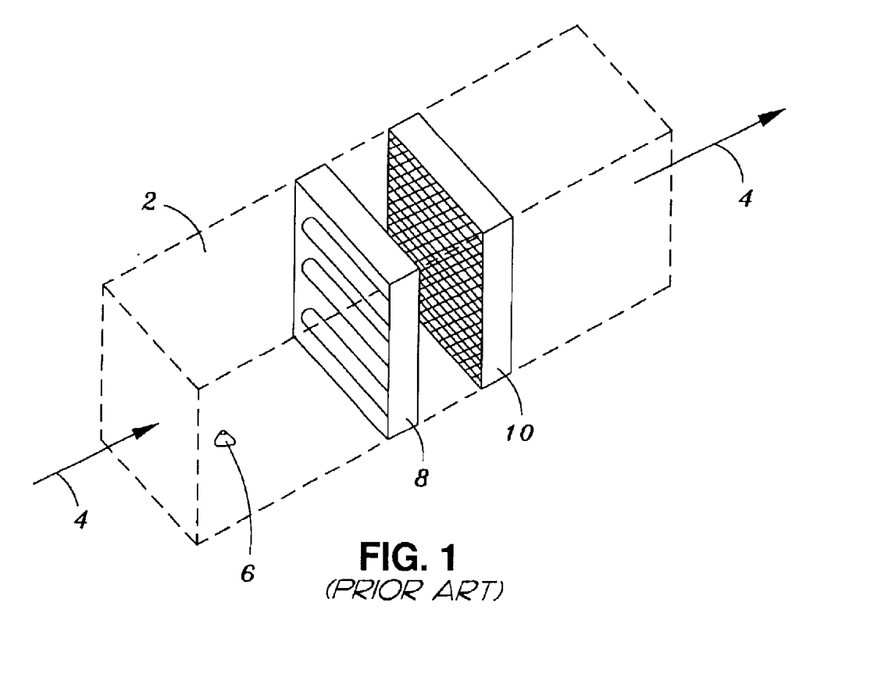
FIG. 1 is a diagram of a prior art photocatalytic air filter designed for use in a building air duct.

Referring to FIG. 1, a prior art photocatalytic air filter designed for use in a building air duct is shown. Air flows through a duct 2 in a direction 4. The air is humidified by a humidifier 6. Subsequent to humidification, the air passes through a bank of ultraviolet lights 8 and a mesh 10. Water in the form of air humidity is perpetually carried to the mesh 10 on the air flowing through the mesh. The bank of ultraviolet lights 8 is operative to cast ultraviolet light upon the mesh 10. The mesh 10 is itself coated with a transition metal oxide, such as $TiO_2$. The transition metal oxide and water undergo a photocatalytic reaction in the presence of the ultraviolet light to create free hydroxyl groups. The free hydroxyl groups have been shown to have a microbicidal effect. Microcontaminants on the air stream are therefore actively eliminated as the air passes through the mesh 10. As discussed above, the design possibilities of this system are limited by the need to illuminate the $TiO_2$ coated surface with ultraviolet light. Specifically, because the mesh 10 is not substantially transmissive of ultraviolet light, any surface area to be coated with $TiO_2$ must face the bank of ultraviolet lights 8. Therefore, the only way to increase the available surface area of the mesh 10 is to introduce a more complex design, for instance by substituting a multifaceted grill. A practical limit is also imposed upon the maximum surface area. Simplicity and pressure drop characteristics suffer accordingly.

Figure 2A:
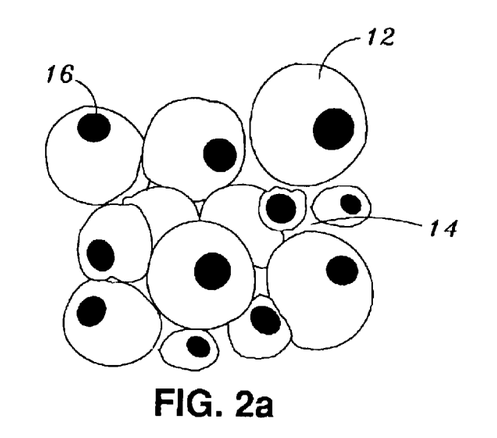
FIG. 2a is a microscopic level view of sintered glass beads comprised by the filter system of the present invention.

Referring to FIG. 2a, a microscopic level view of sintered glass beads comprised by the filter system of the present invention is shown. A plurality of glass beads 12 are sintered and have pores 14 formed therebetween to allow air to flow therethrough. Sintering is a process known to those in the art in which the glass beads 12 are placed together and subjected to a combination of heat and pressure. The heat and pressure cause the glass beads 12 to cohere. In the preferred embodiment of the present invention, the sintering process is accomplished at a temperature of above the transition temperature of the glass beads 12. When sintering at above the transition temperature of the glass beads 12, the sintering process is accomplished relatively quickly. In experimental trials, sintering took between 15 to 60 minutes. The glass beads 12 are sintered at above their transition temperature because it was discovered that sintering at below the transition temperature results in an undesirable degree of devitrification of the glass beads 12. Devitrification is a process whereby crystals are formed in the glass beads 12. Crystal formation increases the index of refraction of the glass beads 12 and thus, increases the degree to which they are dispersive of ultraviolet light. The preferred embodiment of the present invention therefore comprises glass beads 12 which are substantially non-crystalline to mitigate dispersion of ultraviolet light within the glass beads 12, to facilitate penetration of the glass beads thereby.

When sintered, the glass beads 12 essentially form a single, microporous glass structure. Said structure may be highly porous, having for instance a degree of porosity in the region of 25%. In this respect, the surface area of the glass beads 12 per thickness of the structure is high in comparison with what it would be if there were no pores formed therebetween. Because pressure drop is inversely proportional to the surface area of the glass beads 12, pressure drop of the filter system of the present invention benefits thereby. In other words, the sintered glass beads 12 have an advantageously high surface area, much the same as in a HEPA filter. The pores 14 follow paths between the glass beads 12 which can be characterized as having multiplicitous interstices and a high frequency of irregular turns and twists. Flow of air through pores of this nature results in high capture efficiency as the air is subjected to continual friction against itself and buffeting against the glass beads 12.

It is furthermore worth noting that depending upon the application, the size of the pores 14 may be selected by means as known to those in the art in order to provide a simple physical filtering effect as well as the active destruction effect described below.

Figure 2B:
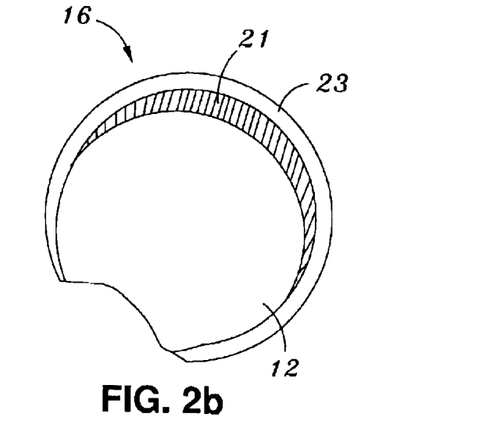

Referring now FIG. 2b, a cross-section of one of the glass beads 12 is shown. The filter system comprises a coating 16 formed on at least a portion of the glass beads 12 of transition metal oxide 21 and water 23. Titanium dioxide ($TiO_2$) is hereinafter used as an example of a transition metal oxide, but other transition metal oxides could be used. Deposition of the $TiO_2$ can be accomplished by means as known to those in the art. In experimental runs, a liquid suspension of $TiO_2$ was created and caused to flow between the glass beads 12 subsequent to sintering, thereby depositing $TiO_2$ over the surface of the glass beads 12. Water can also be deposited by various means, and can be provided from various sources. Depending on the environment in which the filter is to be used and the type of filter, the water could be provided by ambient humidity. Alternatively, the filter system could comprise a humidifying device of some kind.

Figure 3:
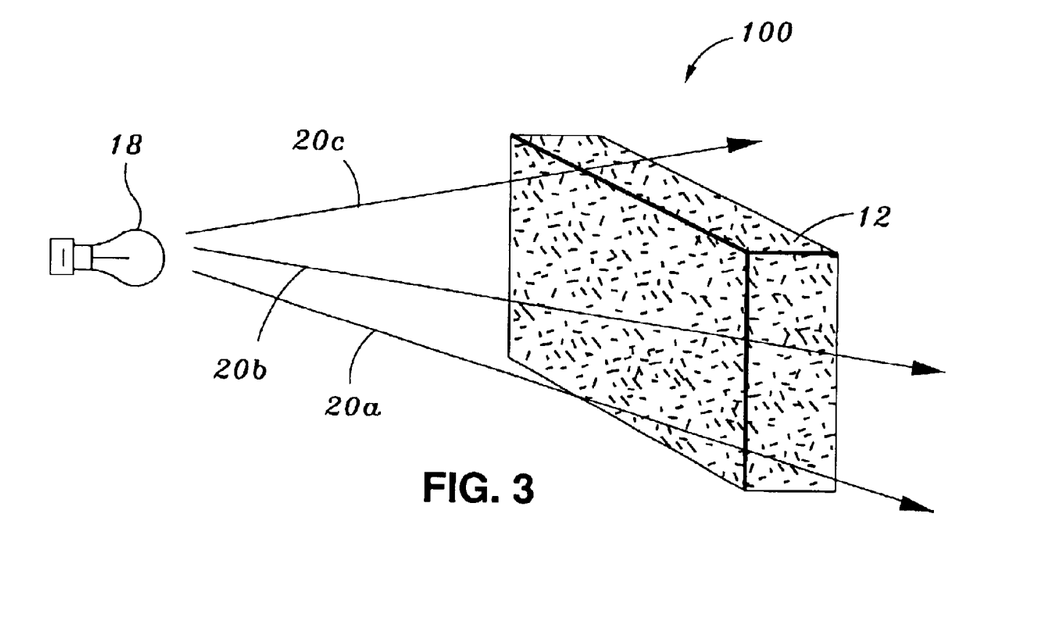
FIG. 3 is a view of the complete filter system, including ultraviolet light source.

Referring now to FIG. 3, the entire filter system 100 is shown. The filter system 100 can be seen to further comprise an ultraviolet light source 18. Depending again upon the environment and application of the filter system 100, the ultraviolet light source 18 could be the sun. Alternatively, it could be an artificial light source. The ultraviolet light source 18 is operative to illuminate the glass beads 12. Specifically, the ultraviolet light source 18 casts rays of ultraviolet light 20a,b,c upon the entirety of the microporous glass structure defined by the sintered glass beads 12. Because the glass beads 12 are substantially transmissive of ultraviolet light, at least some of the rays of ultraviolet light 20a,b,c are able to pass the more proximate of the glass beads 12 to reach the more distal glass beads 12. Accordingly, despite the fact that the glass beads 12 may be sintered in such a way as to define a structure having substantial depth (and accordingly higher surface area), the entire surface area of all of the glass beads 12 receives illumination from the ultraviolet light source 18. When the coating 16 on the glass beads 12 receives the ultraviolet light rays 20a,b,c, a photocatalysis reaction is facilitated between the $TiO_2$ and the water of the coating 16. The photocatalysis reaction produces free hydroxyl groups. As discussed above, the free hydroxyl groups have been shown to have microbicidal properties. Air passing between the glass beads 12 is subjected to contact with said free hydroxyl groups and, accordingly, microcontaminants in the air are actively destroyed.

Figure 4:
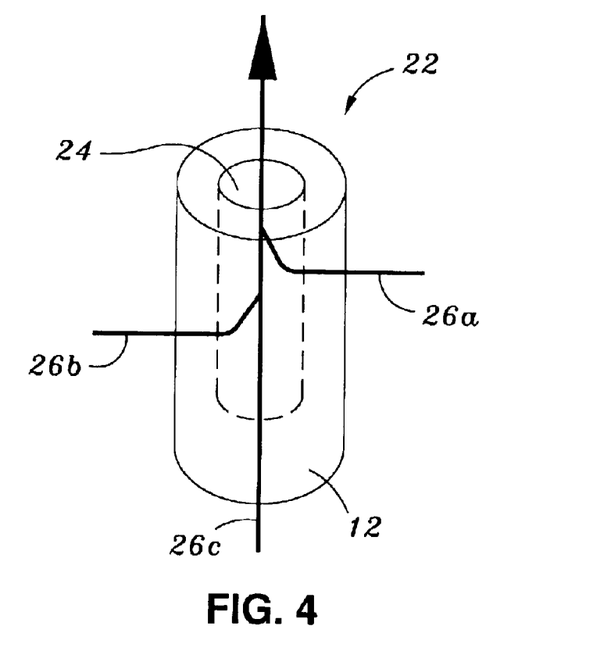
FIG. 4 is a view of an advantageous filter configuration.
Figure 5:
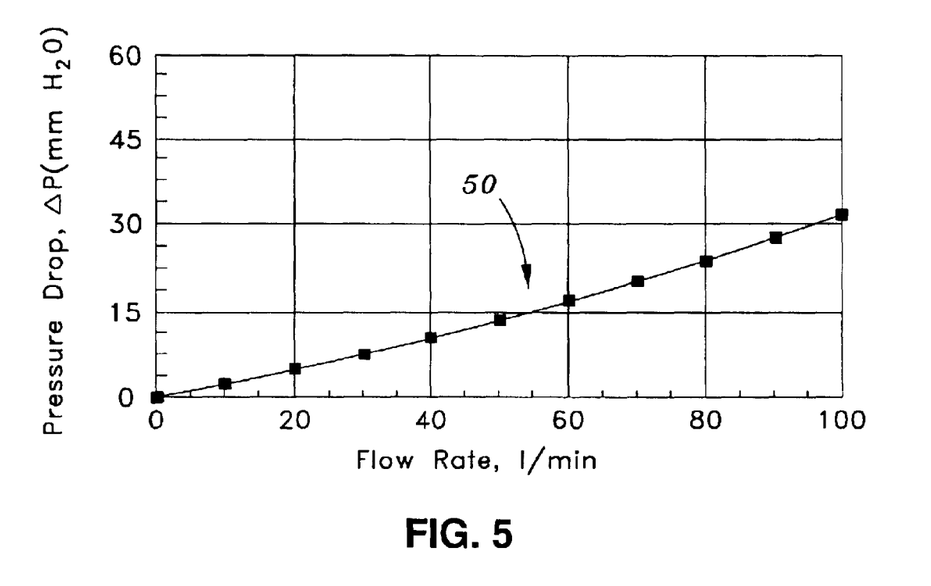
FIG. 5 is a plot of flow rate against pressure drop for a hollow cylindrical filter designed in accordance with the present invention having a wall thickness of 2 cm. and a height of 15 cm.

Referring now to FIG. 4, it is demonstrated how the design of a filter 22 comprised by the filter system 100 (FIG. 3) of the present invention may be selected advantageously in accordance with techniques known to those in the art. As discussed above, the surface area of the glass beads 12 is important to performance. The surface area defined by the filter's 22 outer surface itself is also important, however. In this example, a cylindrical filter 22 having a smaller cylindrical opening 24 is constructed. Air flows in directions 26a,b,c between the glass beads 12 and into the opening 24 to be drawn out through the top of the opening. According to simple principles of geometry, this configuration has an advantageously high surface area. The pressure drop of this configuration will therefore be desirably low. If the pressure drop of the filter 22 is below 40 mm $H_2O$ at 85 liters per minute, unassisted human breathing through the filter 22 is possible. One embodiment of the present invention therefore comprises a filter 22 having a pressure drop under that limit. Referring to FIG. 5, a plot 50 of flow rate against pressure drop is shown for a hollow cylindrical filter having a wall thickness of 2 cm and a height of 15 cm. From the plot it can be seen that at 85 liters per minute, the filter has a pressure drop of well below 40 mm $H_2O$. Accordingly, unassisted human breathing is possible with this filter. Capture efficiency with filters of 2 cm thickness proved to be greater than 98% at all face velocities. These numbers represent a substantial improvement over the prior art.

Figure 6:
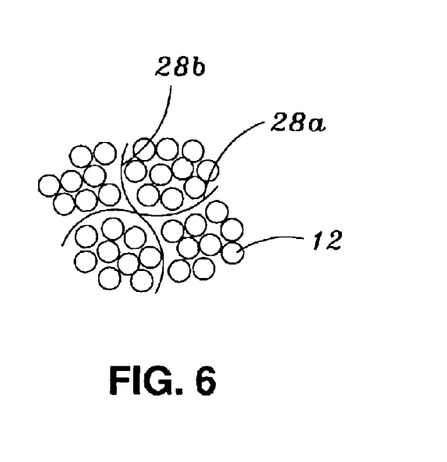
FIG. 6 is a view of a further embodiment in which urethane foam is added prior to sintering in order to create a bimodal pore size distribution.

Referring now to FIG. 6, in accordance with a further embodiment of the present invention, urethane foam 28a,b is inserted between the glass beads 12 prior to sintering. During sintering, the urethane foam 28a,b decomposes and oxidizes. Use of the urethane foam 28a,b results in a bimodal pore size distribution in the finished product. In other words, the resulting structure will have a first group of pores having a first mean pore size, and a second group of pores having a second mean pore size, the second mean pore size being larger than the first mean pore size. This appears to result in more tortuous paths between the glass beads 12, increasing capture efficiency.

Figure 7:
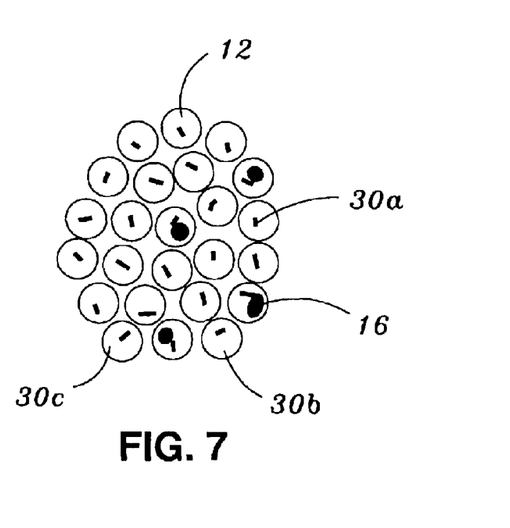
FIG. 7 is a view of still a further embodiment in which particulates are added during sintering.

Still a further embodiment is shown in FIG. 7, wherein it can be seen that inorganic particulates 30a,b,c may be comprised by the coating 16. The inorganic particulates 30a,b,c may be, for instance, glass particulates or chopped fibers. The addition of the inorganic particulates 30a,b,c alters surface activity and, depending upon the microcontaminants to be filtered, may improve capture efficiency. Of course, the addition of inorganic particulates may be combined with the use of urethane foam as described above.

Figure 8:
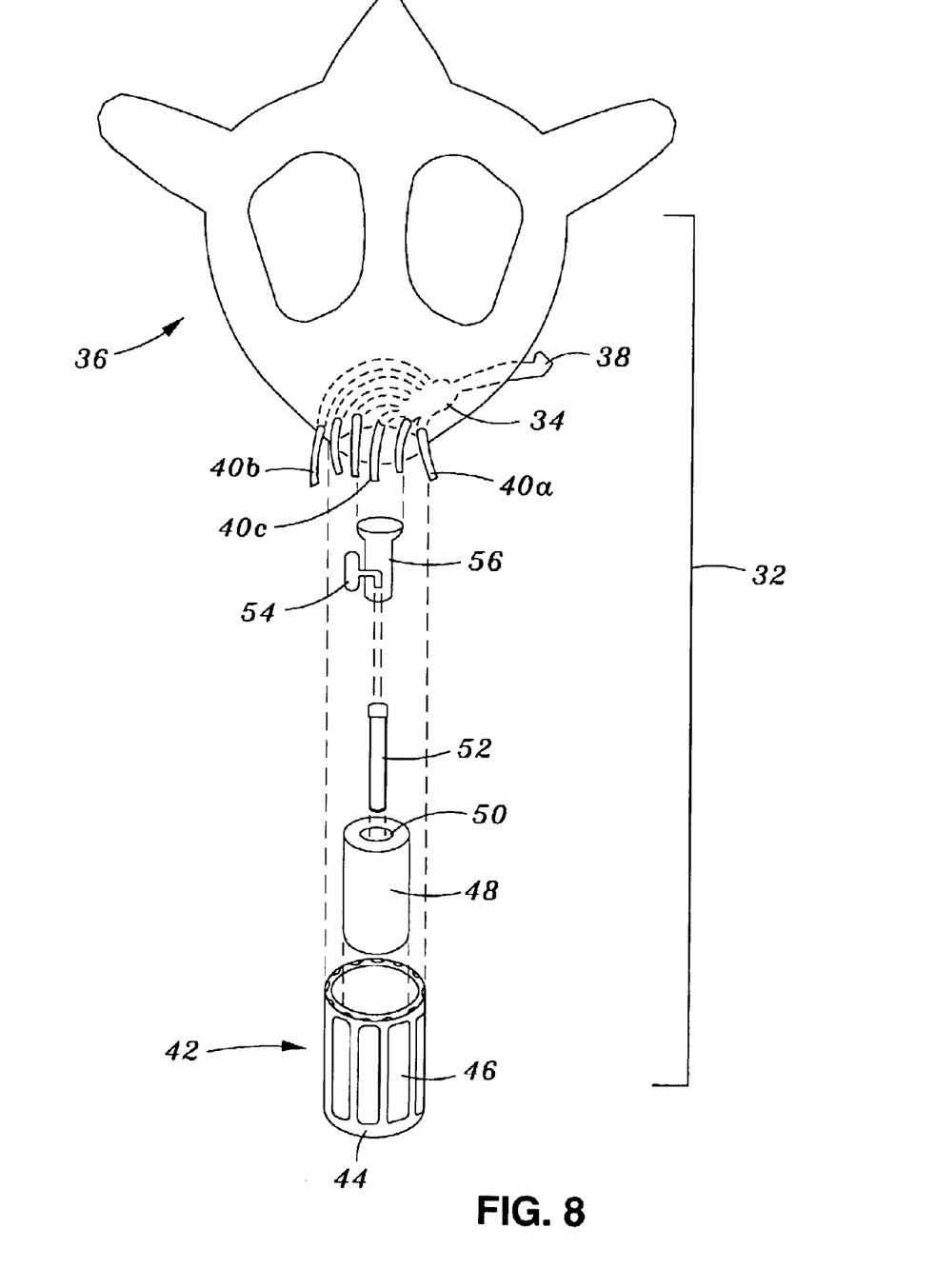
FIG. 8 is a exploded view of a filter mask.

Referring now to FIG. 8, an exploded view of a filter mask 32 in accordance with the present invention is shown. The filter mask 32 comprises a reservoir 34 disposed within a mask element 36. The reservoir 34 is operative to store water, which may be replenished through a connector 38. Attached to the reservoir are a plurality of tubes 40a,b,c. Each tube 40a,b,c has a small enough diameter that water may be drawn along it by means of capillary action, without any need for a pump. Of course, in an alternate embodiment, a pump could be employed. Each tube 40a,b,c attaches to a humidifying device 42. The humidifying device 42 comprises a housing 44 which contains an absorptive element 46. The absorptive element 46 may be composed of any material which will absorb water, such as layered cloth or sponge. The ends of the tubes 40a,b,c are disposed immediately adjacent to the absorptive element 46. The absorptive element 46 will therefore draw water from the reservoir 34 through the tubes 40a,b,c to become wet. As the amount of water retained by the absorptive element 46 increases, its drawing force upon the water in the reservoir 34 drops off until it is not sufficient to actuate the aforementioned capillary action, at which point water draw stops. The size of the tubes 40a,b,c, absorptivity of the absorptive element 46, and other variables may be selected by means known to those in the art in order to achieve this end. When the filter mask 32 is in use, air is drawn by a user's own breathing action through the absorptive element 46 and subsequently through a glass structure 48 of sintered glass beads having a deposition of titanium oxide as described in detail above. As the air passes through the absorbative element, it gathers water from the absorbative element. The glass structure 48 of this embodiment is of a configuration similar to that disclosed in FIG. 4, and has an opening 50 for the flow of air therethrough. The opening is partially, but not entirely occupied by an ultraviolet lamp 52 which casts light from the inside of the glass structure 48 onto the entirety of the glass structure 48. Power to the ultraviolet lamp 52 is provided by a battery 54. The light being provided by the ultraviolet lamp 52, and the necessary moisture being carried on the air as it passes through the glass structure 48, the air is filtered in the method described in detail above. It then flows through a retainer 56 and into the mask element 36 to be inhaled by the user. Exhaled air follows the reverse path. It is worth noting that in the embodiment shown, moisture may travel by means of air between the absorptive element 46 and the user's lungs. Depending on the embodiment, this might be desirable inasmuch as moisture could be carried from the user's own body to the glass structure 48, eliminating or reducing reliance upon the reservoir 34. Alternatively, a moisture isolater of some type could also be comprised by the filter mask 36.

Figure 9:
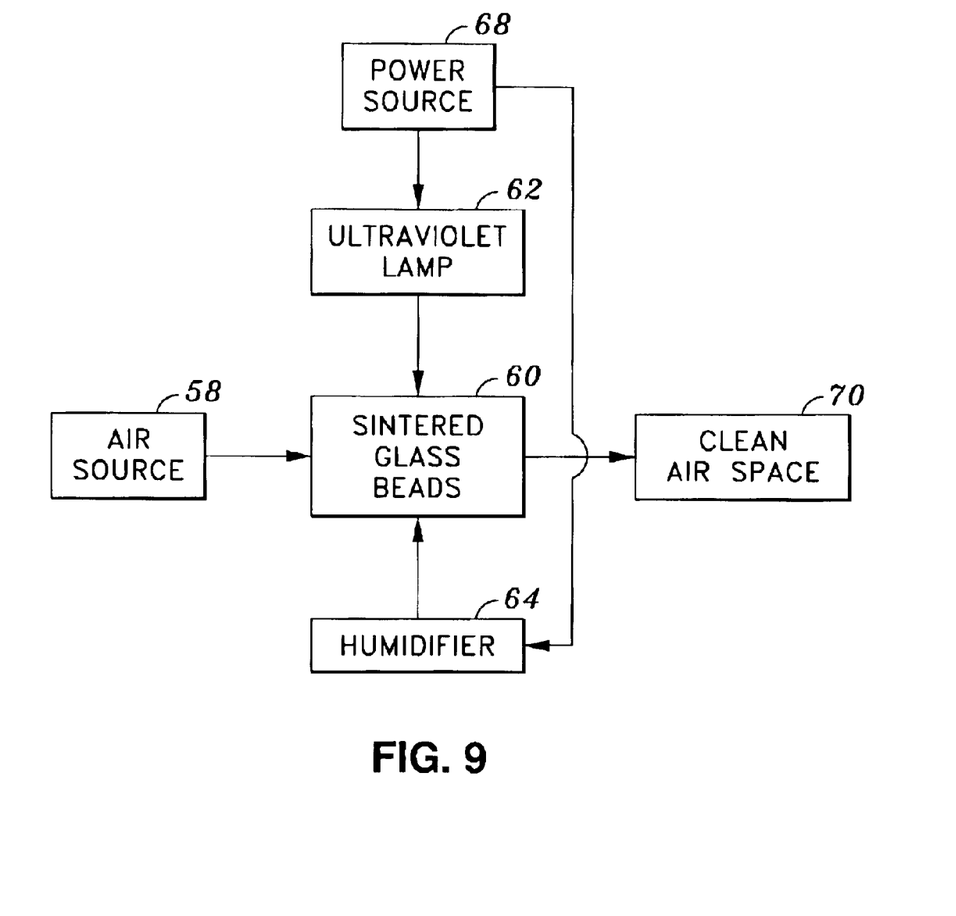
FIG. 9 is a basic block diagram of the present invention.
Figure 10:
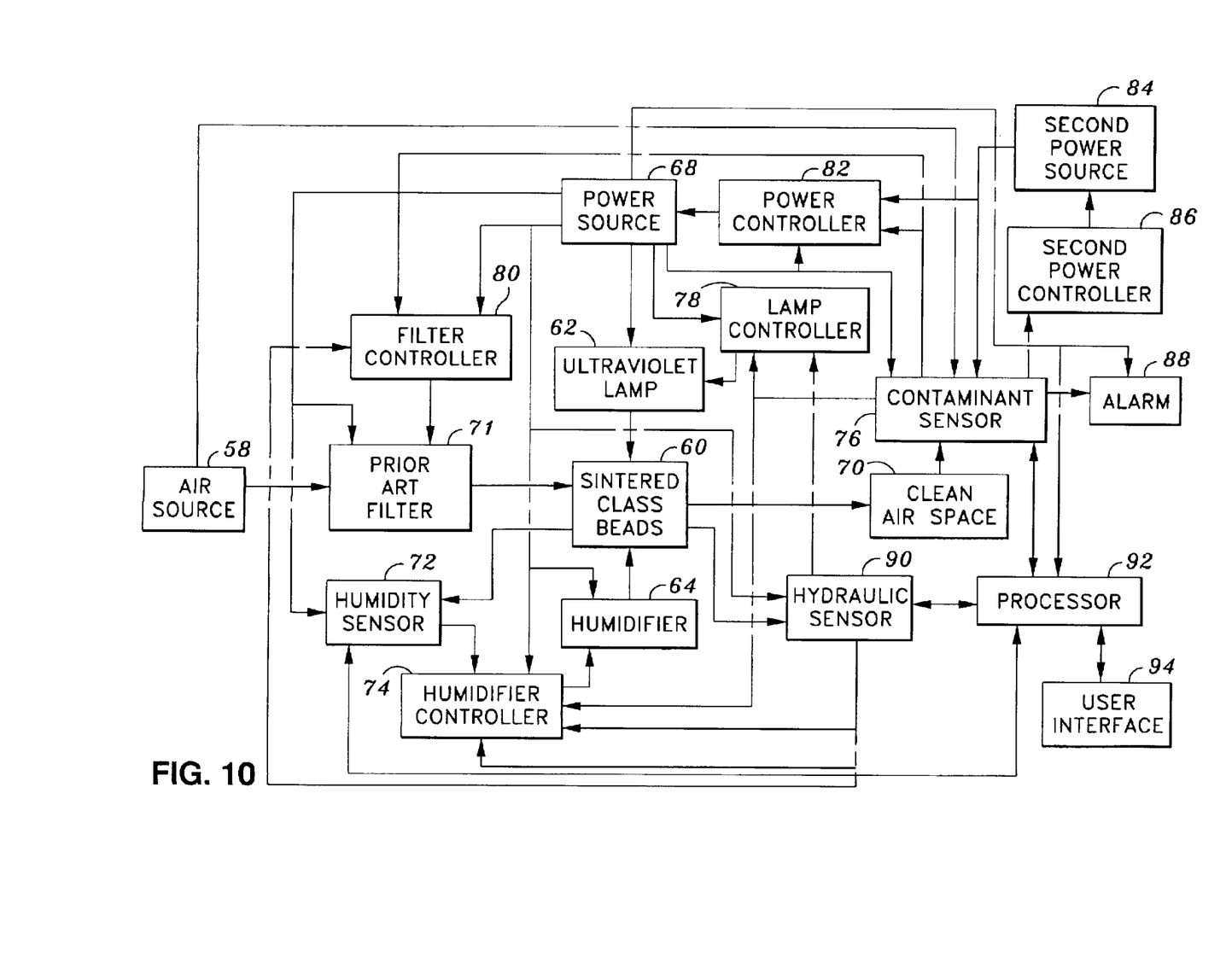
FIG. 10 is a more detailed block diagram illustrating additional structures and functionality that may be incorporated within the present invention.

FIGS. 9 and 10 illustrate how the filtering system of the present invention may be combined with basic system implementation techniques to create a variety of embodiments useful for a variety of applications. Referring to FIG. 9, a relatively simple embodiment is shown. Air from an air source 58 flow through sintered glass beads 60. The sintered glass beads 60 are provided ultraviolet light by an ultraviolet lamp 62. They are provided with water by a humidifier 64. The ultraviolet lamp 62 and humidifier 64 are powered by a power source 68, such as a battery. As air flows through the sintered glass beads 60 it is filtered in the method described above, after which it flows into a clean air space 70 from which a user may breathe.

FIG. 10 illustrates a variety of possible complications configured to provide a variety of additional features. For instance, the system may comprise a prior art filter 71. The prior art filter 71 could be an activated carbon filter, ionic filter, HEPA filter, or any other type of filter known in the art. Air from the air source 58 is filtered by the prior art filter 71 prior to reaching the sintered glass beads 60. This might be desirable, for instance, if it were expected that in the application involved exposure to a high amount of relatively large contaminants, such as ash or dust. The large contaminants could clog the sintered glass beads 60, which is easily prevented by the addition of the prior art filter 71. In this respect, multiple filters may be comprised by the system as in prior art mechanical filters.

The system may also comprise a humidity sensor 72, powered by the power source 68, which is capable of sensing a level of humidity in the structure defined by the sintered glass beads 60. The humidity sensor 72 is operative to send data regarding the humidity level to a humidifier controller 74 also powered by the power source 68. The humidifier control 74 is operative to control the humidifier 64 by increasing or decreasing the amount of humidity provided by the humidifier 64, in response to the data received from the humidity sensor 72. In this respect, the humidity sensor 72, humidifier controller 74, and humidifier 64 may, for instance, operate in a feedback loop in order to maintain a substantially constant level of humidity in the sintered glass beads 60.

The system could further comprise a contaminant sensor 76 powered by the power source 68. The contaminant sensor 76 is operative to detect a level of contamination in the clean air space 70. The contaminant sensor 76 generates data regarding the level of contamination and sends it to the humidifier controller 74, a lamp controller 78, and/or a filter controller 80 all powered by the power source 68. The lamp controller 78 is operative to control the ultraviolet lamp 62 by adjusting the level of ultraviolet light output of the ultraviolet lamp 62. The filter controller 80 is operative to regulate the operation of the prior art filter 71. In this respect, because the contaminant sensor 76 sends data to the humidifier controller 74, lamp controller 78, and/or filter controller 80, the controllers 74,78,80 may control their respective functional devices 62,64,71 in response to the level of contaminants in the clean air space 70. For instance, the controllers 74,78,80 could operate to increase the activity of the ultraviolet lamp 62, humidifier 64, and prior art filter 71 in response to relatively higher contaminant levels, and decrease them in response to relatively lower contaminant levels. This could have the advantage of saving power and increasing the life span of periodically fallible components such as the ultraviolet lamp 62.

The level of contamination sensed by the contaminant sensor 76 could alternatively or also be a level of contamination of the air source 58 instead of the clean air space 70, because it may be desirable to send data to the lamp controller 78, humidifier controller 74, and/or prior art filter 71 in response to this level of contamination as well. For instance, it may be expected that the system will normally operate in relatively uncontaminated environments. If so, it might be desirable to leave the system off entirely during normal circumstances. To this end, the contaminant sensor 76 may be operative to send data to a power controller 82 powered by the power source 68. The power controller is operative to control the power source 68. For instance, the system could be configured so that when the contaminant sensor 76 detects contamination in the air source 58 below a selected level, the power controller 82 turns off the power source 68. Once the contaminant sensor 76 detected a higher level of contamination, the power source 68 could be turned back on. A second power source 84 could be provided to provide power to the contaminant sensor 76 and power controller 82 while the power source 68 was off, and could itself be turned off by a second power controller 86 when not needed. In another logical configuration, when contaminant levels are beneath the selected level, the ultraviolet lamp 62 and humidifier 64 are turned off, but the prior art filter 71 remains on. In this configuration, therefore, the system acts as a prior art filter until a certain level of contamination is detected, whereupon the system also acts as a photocatalytic filter.

At this point, it may be desirable to activate an alarm 88 powered by the power source 68 in order to alert a user that the system is beginning photocatalytic filtering. This can be accomplished by having the contaminant sensor 76 send data to the alarm 88, and configuring the alarm to activate in response to the same. Activation of the alarm will alert a user that the system is switching modes of functionality, and furthermore alert the user that he is entering an area in which contamination is relatively high.

The contaminant sensor 76 could further be configured to detect a plurality of contamination types. For instance, the contaminant sensor could be configured to detect and distinguish between contaminants of below a certain size and contaminants of above the certain size. The contaminant sensor 76 could then send data respecting these multiple values to the controllers 74,78,80. The controllers 74,78,80 would then act the control their respective functional devices 62,64,71 in response. For instance, in the event that large contaminant levels were high but low contaminant levels were low, the system could function to use only the prior art filter 71.

The system could further comprise a hydroxl sensor 90 powered by the power source 68 in addition to or instead of the contaminant sensor 76. The hydroxyl sensor 90 is operative to detect the amount of free hydroxyl radicals present in the structure defined by the sintered glass beads 60. The hydroxyl sensor 90 sends data respecting this measurement to the lamp controller 78, humidifier controller 74, and/or prior art filter controller 80. Each controller 74,78,80 is configured to respond to the data by controlling its respective device 64,62,71. For instance, low hydroxyl radical levels indicate either that the system is not producing enough hydroxyl radicals, or that the hydroxyl radicals being produced are being lost—i.e., being used to destroy microcontaminants. In either event, it is desirable to increase the amount of hydroxyl radicals being produced. In this respect, the hydroxyl sensor 90 and associated controllers and devices function in a feedback loop in order to maintain a selected level of hydroxyl radical presence in the sintered glass beads 60.

Further functionality could be accomplished through the use of a processor 92 powered by the power source 68. The processor is configured to receive data from the humidity sensor 72, contaminant sensor 76, and/or hydroxyl sensor 90. Of course, further sensors could be comprised by the system in order to provide additional data to the processor 92. For instance, a power reserve sensor could be connected to the power source 68 and operative to send data to the processor 92 respecting the amount of power left in the power source 68.

The processor 92 is operative to process data received and respond thereto. The processor's 92 response can take any number of forms. The processor 92 is shown having bidirectional connections to the sensors 72,76,90, and accordingly has the ability to send data to any device which the sensors 72,76,90 can themselves send data to and so on down the chain of connections. It is understood, however, that the processor could be connected directly to any device in the system. An obvious use of the processor 92 would be to provide the functions of the controllers 74,78,80, which could then be done away with. However, the processor 92 can also accomplish functions not achievable by multiple individual controllers.

For instance, consider a situation in which a device fails. The humidifier 64 might fail due to depletion of water reserve. In this situation, the humidity sensor 72, hydroxyl sensor 90, and/or contaminant sensor 76 may all be sending data to the humidifier controller 74 that would normally cause the humidifier controller 74 to make the humidifier 64 provide more humidity. Because the humidifier 64 is non-functional in this scenario, however, this will not have the desired effect. By monitoring, for instance, the hydroxyl radical level and the humidity level in combination, the processor 92 will be able to tell that something is wrong with the humidifier 64 without even the need for a water reserve sensor. The processor 92 could respond by shutting off, among other things, the ultraviolet lamp 62 to save power, and running the prior art filter 71 at a higher level in order to compensate.

Other examples of situations in which the processor 92 could prove invaluable abound. For instance, consider a situation in which the contamination level of the air source 58 is low, but the contamination level of the clean air space 70 is high. Because the contamination level of the clean air space 70 is high, the contaminant sensor 76 will send out data configured to cause the system to respond in a more vigorous fashion, as described above. However, a person will readily distinguish that in this situation, contamination is originating from somewhere other than the air source 58, possibly even from the filtering system itself. The processor 92 can compare the values to make a similar distinction. It can then respond by activating an alarm, shutting down the system, or both.

Naturally, the processor 92 could also be connected to user interface 94 to allow interaction between a human user and the processor 92. For instance, it may be of interest to a user to personally monitor data being generated by the sensors 72,76,90. The user interface 94 could comprise a display operative to accomplish this objective. Conversely, the user interface 94 can allow the user to control the system through the processor 92. For instance, if the user has another filtering system at his disposal, he may wish to turn the system off entirely despite high local incidence of contamination. Of course, it will be realized by one skilled in the art that the user interface 94 could communicate directly with various devices in the system other than the processor 92. This would be particularly appropriate in the case of a relatively simple filtering system, e.g. a filter mask as shown in FIG. 8. Such a filter mask might, for instance, comprise a user interface 94 consisting of a single knob. The knob would be operative to increase both the output of the ultraviolet lamp 62 and the output of the humidifier 64.

Further modifications and embodiments will be apparent to those skilled in the art.

What is claimed is:

1. A microbicidal filter system comprising:
   a. a plurality of glass beads sintered above a transition temperature thereof and having pores formed therebetween to allow flow of air therethrough;
   b. a coating of transition metal oxide and water formed on at least a portion of the glass beads; and
   c. an ultraviolet light source operative to illuminate the glass beads, the light source being operative to facilitate a photocatalysis reaction within the coating, producing free hydroxyl groups having microbicidal properties.

2. The microbicidal filter system of claim 1, wherein the glass beads are substantially non-crystalline to mitigate dispersion of ultraviolet light within the glass beads, to facilitate penetration of the glass beads thereby.

3. The microbicidal filter system of claim 1, wherein the water is provided by ambient humidity.

4. The microbicidal filter system of claim 1, wherein the ultraviolet light source is sunlight.

5. The microbicidal filter system of claim 1, wherein pressure drop of the filter system is below 40 mm $H_2O$ at 85 liters per minute in order to allow unassisted human breathing through the filter system.

6. The microbicidal filter system of claim 1, wherein the pores comprise a first pore group having a first mean pore size, and a second pore group having a second mean pore size, the second mean pore size being larger than the first mean pore size.

7. The microbicidal filter system of claim 1, wherein the coating further comprises inorganic particulates.

8. The microbicidal filter system of claim 1, further comprising at least one environmental sensor, operative to sense at least one environmental parameter of the microbicidal filter system and generate at least one value corresponding thereto.

9. The microbicidal filter system of claim 8, wherein the at least one environmental sensor comprises a humidity sensor, operative to sense an amount of water on the glass beads and generate a value corresponding thereto.

10. The microbicidal filter system of claim 8, wherein the at least one environmental sensor comprises a hydroxyl sensor, operative to sense an amount of free hydroxyl radicals present in the pores and generate a value corresponding thereto.

11. The microbicidal filter system of claim 8, wherein the at least one environmental sensor comprises a contaminant sensor, operative to sense at least one level of contamination present in the group of:

a. an air source for the filtering system; and
  b. an enclosed volume of air into which air flowing through the filter system enters;

and generate at least one value corresponding thereto.

12. The microbicidal filter system of claim 11, further comprising an alarm device operative to generate an alarm when the at least one generated value exceeds a selected level.

13. The microbicidal filter system of claim 8, further comprising a humidifier, operative to deposit water onto the glass beads.

14. The microbicidal filter system of claim 13, further comprising a controller operative to regulate an amount of water deposited by the humidifier in response to the at least one generated value.

15. The microbicidal filter system of claim 8, further comprising a controller operative to regulate a light intensity of the ultraviolet light source in response to the at least one generated value.

16. The microbicidal filter system of claim 15, further comprising a controller operative to regulate at least one operational parameter of the contaminant pre-filter in response to the at least one generated value.

17. The microbicidal filter system of claim 8, further comprising a contaminant pre-filter.

18. The microbicidal filter system of claim 8, further comprising a processor operative to regulate at least one operational parameter of the filter system in response to the at least one generated value.

19. The microbicidal filter system of claim 8, further comprising a user interface, operative to display the at least one generated value for human operator.

20. The microbicidal filter system of claim 19, wherein the user interface is further operative to allow the human operator to control at least one operational parameter of the filter system.

21. A method of filtering microbes from air, comprising:

a. sintering a plurality of glass beads generally above a transition temperature thereof to form into a structure having pores to allow flow of air therethrough;
  b. depositing a coating of transition metal oxide and water onto at least a portion of the glass beads; and
  c. illuminating the coating with ultraviolet light, the light being operative to facilitate a photocatalysis reaction within the coating to produce free hydroxyl groups having microbicidal properties.

22. The method of claim 21, wherein the step of depositing a coating of transition metal oxide and water comprises exposing the glass beads to airborne humidity.

23. The method of claim 21, wherein the step of illuminating the coating with ultraviolet light comprises exposing the coating to sunlight.

24. The method of claim 21, further comprising disposing urethane foam between the glass beads before sintering, the urethane foam decomposing and oxidizing during sintering.

25. The method of claim 21, further comprising disposing inorganic particulates on the glass beads.

* * * * *